United States Patent
Bazin et al.

(10) Patent No.: US 8,360,973 B2
(45) Date of Patent: Jan. 29, 2013

(54) PROCESS FOR ACQUIRING SCANNED IMAGE DATA RELATING TO AN EXTERNAL BODY PORTION AND/OR A PRODUCT APPLIED THERETO

(75) Inventors: Roland Bazin, Bièvres (FR); Eric Doublet, Villejuif (FR)

(73) Assignee: L'Oreal, Paris (FR)

( * ) Notice: Subject to any disclaimer, the term of this patent is extended or adjusted under 35 U.S.C. 154(b) by 1095 days.

(21) Appl. No.: 09/725,048

(22) Filed: Nov. 29, 2000

(65) Prior Publication Data

US 2002/0065456 A1    May 30, 2002

(51) Int. Cl.
*A61B 5/00* (2006.01)
*G06K 9/00* (2006.01)

(52) U.S. Cl. ........................................ 600/300; 382/100

(58) Field of Classification Search .................. 604/407; 600/407, 476; 382/100, 128, 132; 424/102, 424/78.03, 702, 703, 402; 536/24.31; 514/562
See application file for complete search history.

(56) References Cited

U.S. PATENT DOCUMENTS

| | | | |
|---|---|---|---|
| 4,738,537 A | | 4/1988 | Yquel et al. |
| 4,788,593 A | * | 11/1988 | Ovshinsky et al. ............ 348/294 |
| 4,894,547 A | * | 1/1990 | Leffell et al. ............... 250/461.2 |
| 5,097,024 A | | 3/1992 | Hodes et al. |
| 5,211,894 A | * | 5/1993 | Groh et al. ................... 264/40.1 |
| 5,343,536 A | | 8/1994 | Groh |
| 5,549,476 A | * | 8/1996 | Stern ............................. 433/223 |
| 5,691,380 A | | 11/1997 | Mason et al. |
| 5,785,960 A | | 7/1998 | Rigg et al. |
| 5,796,862 A | | 8/1998 | Pawlicki et al. |
| 5,878,746 A | * | 3/1999 | Lemelson et al. ............. 128/920 |
| 5,897,857 A | | 4/1999 | Hillebrand et al. |

(Continued)

FOREIGN PATENT DOCUMENTS

| | | |
|---|---|---|
| DE | 23 53 224 | 5/1975 |
| DE | 43 37 528 | 7/1995 |

(Continued)

OTHER PUBLICATIONS

Mu unveils pilot program for distance plant diagnosis (Dec. 15, 1998).*

(Continued)

*Primary Examiner* — Annette Dixon
(74) *Attorney, Agent, or Firm* — Connolly Bove Lodge & Hutz LLP

(57) ABSTRACT

A process is disclosed for acquiring scanned image data relating to an external body portion and/or a product applied to the external body portion. The process includes placing a transfer member in contact with an external portion of an individual to obtain a transfer image on the transfer member. The transfer image of the transfer member is scanned with an optical image scanner to obtain scanned image data. The scanned image data may be sent from a first computer associated with the scanner to a second computer at a remote location. An image corresponding to the scanned image data may be displayed and viewed to analyze a characteristic of the external body portion and/or a characteristic of a product applied to the external body portion. The process may also involve determining a recommendation of a treatment for the external portion and providing this recommendation. Another aspect relates to evaluating the product applied to the external body portion. In addition, the process may include monitoring the status of the external body portion during treatment.

23 Claims, 12 Drawing Sheets

U.S. PATENT DOCUMENTS

| | | | |
|---|---|---|---|
| 5,944,667 A | | 8/1999 | Leveque et al. |
| 5,985,300 A | | 11/1999 | Crotty et al. |
| 5,991,433 A | | 11/1999 | Osanai et al. |
| 6,101,407 A | * | 8/2000 | Groezinger ............... 366/160.1 |
| 6,106,818 A | | 8/2000 | Dulog et al. |
| 6,178,255 B1 | * | 1/2001 | Scott et al. ....................... 356/71 |
| 6,195,475 B1 | | 2/2001 | Beausoleil, Jr. et al. |
| 6,217,334 B1 | * | 4/2001 | Hultgren ........................ 433/215 |
| 6,230,043 B1 | * | 5/2001 | Johnson ........................... 360/18 |
| 6,241,668 B1 | * | 6/2001 | Herzog .......................... 600/407 |
| 6,289,115 B1 | * | 9/2001 | Takeo ............................ 128/920 |
| 6,296,880 B1 | * | 10/2001 | Murad ........................... 424/616 |
| 6,318,994 B1 | * | 11/2001 | Chishti et al. .................... 433/24 |
| 6,355,439 B1 | * | 3/2002 | Chung et al. ...................... 435/6 |
| 6,379,306 B1 | * | 4/2002 | Washburn et al. ............. 600/454 |
| 6,418,334 B1 | * | 7/2002 | Unger et al. .................. 128/922 |
| 6,533,971 B1 | * | 3/2003 | Stess et al. .................... 264/40.1 |
| 6,571,003 B1 | * | 5/2003 | Hillebrand et al. ............ 382/118 |
| 6,640,130 B1 | * | 10/2003 | Freeman et al. ............... 600/474 |
| 6,801,343 B1 | * | 10/2004 | Sheng ............................ 358/474 |
| 2002/0016539 A1 | | 2/2002 | Michaelis et al. |
| 2002/0046472 A1 | * | 4/2002 | Tadin ............................... 33/515 |
| 2002/0138923 A1 | * | 10/2002 | Shaffeeullah ................ 12/142 N |
| 2003/0065278 A1 | * | 4/2003 | Rubinstenn et al. ........... 600/587 |
| 2003/0074174 A1 | * | 4/2003 | Fu et al. .......................... 703/13 |
| 2003/0099383 A1 | * | 5/2003 | Lefebvre ........................ 382/128 |
| 2003/0108228 A1 | * | 6/2003 | Garnier .......................... 382/128 |

FOREIGN PATENT DOCUMENTS

| | | |
|---|---|---|
| DE | 29616158 U1 * | 11/1996 |
| DE | 200 10 292 | 11/2000 |
| EP | 293083 A2 * | 11/1988 |
| EP | 1 169 964 | 1/2002 |
| FR | 2736450 A3 * | 1/1997 |
| GB | 2 288 511 | 10/1995 |
| JP | 07274996 A * | 10/1995 |
| WO | 95/34280 | 12/1995 |
| WO | WO 95/34280 | 12/1995 |
| WO | 97/21423 | 6/1997 |
| WO | WO 97/21423 | 6/1997 |
| WO | WO 97/21979 | 6/1997 |
| WO | WO 97/29686 | 8/1997 |
| WO | 00/76398 | 12/2000 |
| WO | WO 00/76398 | 12/2000 |
| WO | WO 01/75586 | 10/2001 |

OTHER PUBLICATIONS

My Sweet Maby Zachary (May 10, 1998).*
Internet citation of Presentation #135 (Nov. 2, 2000).*
Kvedar, J.C. et al. (1999). Teledermatology in a Capitated Delivery System Using Distributed Information Architecture: Design and Development. Telemedicine Journal, 5(4), 357-366.*
"Rapid 3D Scanner Revolutionizes Podiatrics", Pedal Scanner, www.cyberware.com/news/pressReleases/pr003.html, Oct. 4, 1991.
"Optical Scanner", Webopedia Definition and Links, http://webopedia.internet.com/TERM/o/optical_scanner.html, Nov. 6, 1997.
"Footcare Express: The Nation's First One-Stop Footshop", Footcare Express—Press Release, www.footcareexpress.com/press/OneStop.htm.
"Welcome to Virtual Makeover com", www.virtualmakeover.com.
"Scan Your Palm", Spirituality: Palm Reading—Scan Your Palm, www.ofesite.com/spirit/palm/scan.htm.
Rebecca Quick, "Getting the Right Fit—Hips and All", The Walls Street Journal, Marketplace, Oct. 18, 2000.
"Palm Readings", http://magzine.gurl.com/where/palm/sendus.html.
Co-pending U.S. Appl. No. 09/725,049; Title: Process for Diagnosing Conditions of External Body Portions and Features of Products Applied Thereto Inventor(s): Roland Bazin et al. filed Nov. 29, 2000.
English language Derwent Abstract of DE 23 53 224, May 7, 1975.
English language Derwent Abstract of DE 43 37 528, Jul. 20, 1995.
Office Actions dated Apr. 15, 2002; Jul. 31, 2002; Jan. 3, 2003; Jun. 19, 2003; Sep. 16, 2003 for U.S. Appl. No. 09/725,049, filed Nov. 29, 2000.
Patent Abstracts of Japan, English abstract for JP 2002-119512.

* cited by examiner

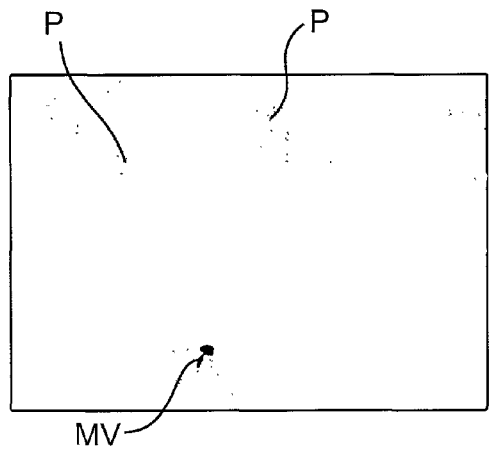 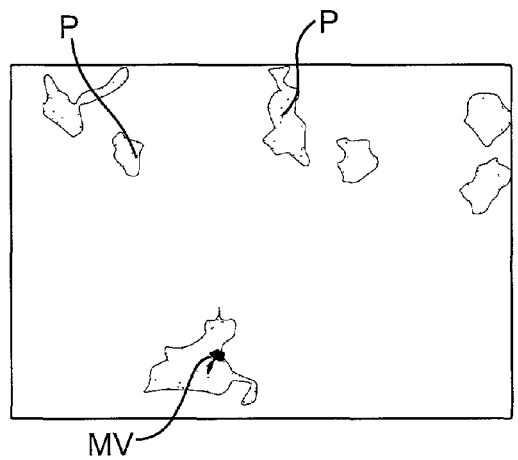
FIG. 10a  FIG. 10b
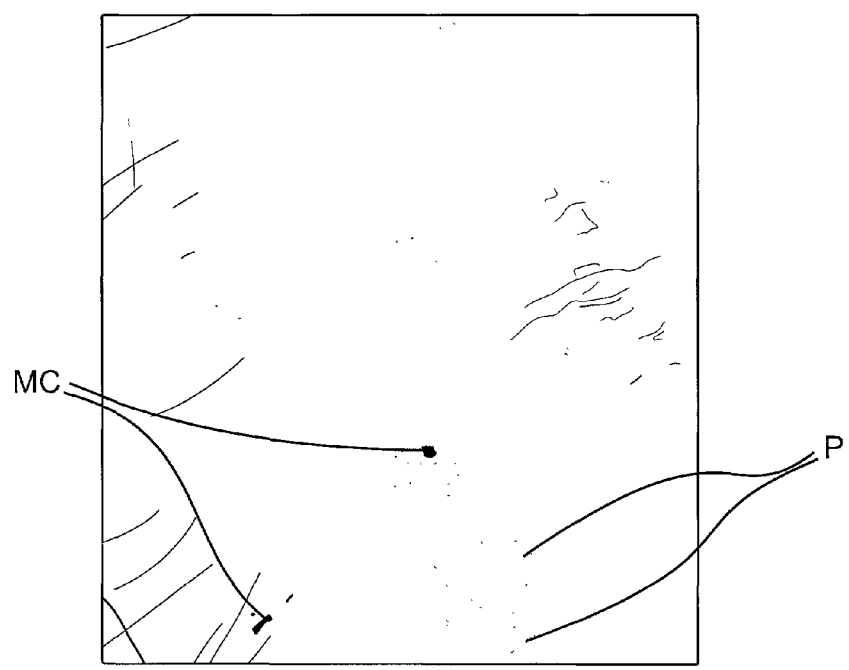
FIG. 11

PROCESS FOR ACQUIRING SCANNED IMAGE DATA RELATING TO AN EXTERNAL BODY PORTION AND/OR A PRODUCT APPLIED THERETO

BACKGROUND OF THE INVENTION

1. Field of the Invention

The present invention relates to a process for acquiring scanned image data relating to an external body portion and/or a product applied thereto, wherein the process involves the use of a transfer member. Such a process could include sending of the scanned information from a first location to a second location remote from the first location. Another aspect of the present invention relates a process for providing a treatment recommendation for the external body portion and/or monitoring of the external body portion. An additional aspect relates to evaluating a product.

2. Description of Related Art

Accurate diagnosis of cosmetic and dermatological related conditions often requires consultations with professionals having the requisite level of proper skill and training. In the past, such consultations required the individual seeking advice to travel to a site and conduct a personal meeting with a professional who would visualize the individual's skin condition, for example, sometimes with special instruments, and prescribe a corrective treatment plan involving one or more cosmetic and/or dermatological products.

Recently, advances in technology have led to a number of attempts at obviating the need for some of these personal, face-to-face meetings requiring travel. In particular, some consultants provide remote cosmetic or dermatological consultations where the individual in need of the consultation can be located at a geographic location different from that of the skilled cosmetician or dermatologist. These attempts have been primarily limited because there has been no easy way of sending all of the necessary information to the remote professional.

GB 2 288 511 discloses a method and apparatus for use in diagnosing medical conditions, such as skin conditions, where there are visual symptoms. This reference discloses operating either a video camera, a camcorder, or a digital still camera to generate an electrical signal that is digitized, compressed, and transmitted to an expert consultant, such as a dermatologist. This technique, however, suffers from a number of drawbacks and limitations. In particular, it is time consuming to operate the video camera, run the software necessary to digitize and compress the image captured by the camera, and then send the compressed image to the consultant. An even more significant limitation relates to the fact that there is no easy way to standardize the image. For example, incorrect lighting, inferior equipment, non-uniform cameras and software programs, incorrect camera operation, or other variables may produce a video image that does not clearly show all of the details of the original area that was recorded. In some cases, the video image submitted to the remote professional might be either completely unusable or result in an incorrect evaluation being made.

Another more simplistic approach involves a consumer filling out a preestablished questionnaire and then sending the completed questionnaire (via a delivery service or the Internet) to a cosmetic product distributor that suggests one or more cosmetic products after reviewing the information provided on the completed questionnaire. Such a process can provide general information useful in advising about some types of basic cosmetic products, but such information is limited by the level of detail in the description provided by the individual and is, therefore, inadequate for many treatments, especially those that are highly specialized and advanced. In addition, both the completion of the questionnaire by the consumer and the evaluation of completed questionnaire by the cosmetic distributor can be time consuming.

In addition to the limitations associated with current means of remote diagnosis, there are also drawbacks associated with some diagnostic methods used during face-to-face consultations with a professional. For example, to examine certain types of skin conditions, some dermatologists use very specialized photographic equipment to obtain a photograph of a skin region being examined. In using one such professional photographic system, called DERMAPHOT, a uniquely designed camera lens is placed in contact with the skin and light is emitted through the lens before taking a photograph of the skin. This technique, however, suffers from a number of drawbacks and limitations. In particular, it is time consuming to properly set up the system, correctly operate the camera, and request a service to develop the film. An even more significant limitation relates to the fact that the specialized photographic equipment is very expensive. Further, the resolution of photographic images obtained with such systems is not always acceptable.

In light of the foregoing, there is a need in the art for improving processes used for collecting data relating to a person's external body portion.

SUMMARY OF THE INVENTION

Accordingly, processes consistent with the present invention preferably may obviate one or more of the limitations of the related art. Such processes have particular advantages in the field of cosmetics and/or dermatology, but may also be used in other areas.

One aspect of the invention includes a process for acquiring scanned image data relating to an external body portion and/or a product applied to the external body portion. The process includes placing a transfer member in contact with an external portion of an individual to obtain a transfer image on the transfer member. The transfer image is scanned with an optical image scanner to obtain scanned image data. This scanned image data is for an image representative of at least one characteristic of the external body portion and/or at least one product applied to the external body portion.

The external portion could be on many different areas of the body of the individual. For example, the external portion could include an area of the skin of the individual, at least one strand of hair of the individual, at least one fingernail of the individual, at least one toe nail of the individual, and at least one tooth of the individual. When the external portion includes the skin of the individual, the external portion may be located on the hand, foot, arm, leg, torso, and/or face (i.e., lips) of the individual. When the external portion includes at least one strand of hair, the strand may be from the scalp, the eyelashes or the eyebrows.

In one possible practice of the process, the transfer image on the transfer member indicates a condition of the external portion. There are many different types of transfer members that could be used. The transfer member could even be part of the image scanner itself. For example, the transfer member could be a window of the scanner that defines the scanner's scanning region.

In one example of the process, the transfer member includes adhesive material provided on a backing, the adhesive material of the transfer member being placed in contact with skin (or another external body portion) and the transfer member being removed from the skin to transfer cells from the skin of the individual to the transfer member. In this example, the amount of cells transferred to the transfer member could be analyzed, based on the scanned data, to diagnose the condition of the dryness of the skin. The adhesive material of the transfer member may be placed in contact with adhesive material of a second transfer member and the transfer members may then be separated to transfer a portion of the skin cells to the second transfer member.

In one other example of the process, the transfer member is placed in contact with an external body portion having a product, such as a cosmetic product, applied thereto, and the image of the scanned image data is representative of at least one characteristic of the product. For example, the external portion could include the lips and the product could be a lip care product or a lip makeup product, such as lipstick.

In an exemplary process where the image of the scanned image data is representative of a product applied to the external body portion, a transfer member in the form of a sheet of material could be placed in contact with lips of the individual and a lip product could be transferred from the lips to the sheet of material. This enables analysis of the non-retention and/or non-transferability characteristics of a makeup product, such as lipstick on the lips.

In another example, the transfer member could be placed in contact with skin, such as facial skin, having foundation makeup applied thereto. Such a process could be used to analyze non-retention and/or non-transferability characteristics of the foundation makeup. For example, when the transfer member is a piece of fabric or an entire article of fabric clothing, such as a blouse, the method could be used to evaluate whether a product causes soiling of clothing and/or whether the product remains on the skin during a period of time.

In a further example, where the transfer member includes a moldable material, the moldable material is placed in contact with the skin of the individual to produce, on the moldable material, the surface profile of the skin.

In yet another example, where the transfer member is a hair comb or a hair brush, the comb or brush is passed through hair, and the image on the transfer member includes hair strands and/or skin cells.

Still another example involves the use of a transfer member configured to change color in response to a condition of the external portion. For example, the transfer member could be formed of litmus paper.

The above-mentioned mode of scanning using the transfer member may be combined with other scanning modes. For example, the transfer member scanning mode could be combined with a direct scanning mode where an external body portion is directly scanned with the image scanner. These modes could occur either simultaneously or one after the other.

In the direct scanning mode, the external portion of the individual is placed in the vicinity of a scanning region of the scanner, and the external portion is scanned with the image scanner to obtain the scanned image data. The external portion of the individual is preferably placed into contact with the scanning region (i.e., the glass window pane) of the scanner. In one embodiment, the scanner is a flat bed scanner and the external portion of the individual is moved into contact with the scanning region. In another embodiment, the scanner is a hand-held scanner and the scanner is moved into contact with the external portion of the individual. Optionally, a liquid is placed between the external body portion and the scanning region, the liquid altering the index of refraction to improve visualization of the characteristic of the external body portion and/or the product applied thereto. The direct scanning mode may also involve placing a dye and/or a pigment on the external portion to improve viewing of the characteristic.

In one preferred embodiment, a first computer associated with the image scanner is located at a first location, and the process further comprises transferring the scanned image data from the first computer to a second computer located at a second location remote from the first location. The transferring may include transmitting the scanned image data via the Internet, or shipping a data storage medium, such as a CD ROM or computer disk, to the second location.

Other information may also be transferred to the second location. For example, questionnaire answers relating to the condition of the external portion and/or the product applied to the external portion may be transferred to the second location. Billing and/or payment information could also be sent to the second location.

One aspect of the invention relates to a process of analyzing one or more characteristics of an external body portion and/or a product applied thereto. This aspect preferably involves displaying an image corresponding to the scanned image data. The displayed image is preferably viewed to analyze the characteristics. Based on this analysis, a diagnosis of the condition of the external portion and/or an evaluation of the product may be determined.

The characteristics of the external portion that are analyzed are preferably characteristics of non-dermatoglyphic body portions. As used herein, the term "non-dermatoglyphic" relates to an external area of the body substantially free of dermatoglyphs, wherein dermatoglyphs are features that do not change as a person ages. For example, dermatoglyphs are located on the inferior surface of the hand in the form of fingerprints and palm lines. Some examples of characteristics of "non-dermatoglyphic" body portions include wrinkles, crows eyes, blood vessel networks visible through the skin, skin pores, cosmetic materials applied to an external body portion, viewable features of hair strands including roots, viewable features of skin including pigmentations and groups of skin cells, viewable features of fingernails and toe nails, and exteriorly viewable features of teeth.

There are many different characteristics of products that could be analyzed with the process according to the invention. For example, the process could be practiced to analyze product characteristics, such as non-transferability, especially for lipstick and foundation makeup; product coverage (i.e., homogeneity), especially for nail enamel or hair conditioner; brilliancy, especially for nail enamel; coloring, especially for various types of makeup products; greasiness, especially for skin lotions; various interactions between the skin and the product, especially for products designed to make wrinkles less visible and products designed to change transparency of the skin; and thickness or amount of the product on the external portion, especially for hair products such as conditioners.

In another preferred practice of the invention, the process includes sending the scanned image data to a plurality of locations so that the characteristic(s) may be analyzed numerous times.

Another aspect of the process includes monitoring status of the external portion during treatment of the external portion. For example, the monitoring process may include repeating at least the acquiring of the scanned image data. A recommendation for an additional treatment could be provided based on the monitored status. In addition, the individual may be provided with information regarding the effectiveness of the treatment.

A further aspect of the present invention relates to a process for recommending treatment for an external body portion. The characteristics of the external portion are analyzed and one or more treatment recommendations for the external body portion are determined. The treatment recommendation is provided so that the external portion of the individual may be treated according to the recommendation. A second, remotely located computer may at least partially determine the treatment recommendation.

The recommendation could be a recommendation regarding use of a cosmetic product and/or a dermatological product, such as a makeup product, a care product, a hair product, a skin product, and a sun exposure product. For example, it could be a recommendation regarding application of the product to the external portion. Optionally, product ordering information is provided along with the recommendation.

The treatment recommendation may be provided to the individual and/or a treatment provider. This information may be sent via the Internet or any other form of communication means.

Another aspect relates to evaluating a product applied to the external body portion. Such a process involves the analysis of one or more characteristics of a product, such as a cosmetic product.

The process may also involve one or more databases. For example, the process may include collecting information relating to the scanned external portion to form a database for use in diagnoses, treatment recommendation determinations, product evaluations, and product formulations. In another example, the analysis of the characteristic may include comparing an image formed from the scanned image data to at least one image formed from image data stored in an image database.

In another aspect, the scanned image data includes data regarding color of the transfer image. This enables the analysis at the second location to include an evaluation of the color of the characteristic(s).

In yet another aspect, the scanner emits light on the transfer member during scanning. Preferably, the scanner is configured in the form of a scanner for scanning documents.

In a further aspect, a calibration member is scanned along with the image of the transfer member. The calibration member preferably has a predetermined size and/or a predetermined color.

In an even further aspect, the scanned image data includes data relating to multiple scanned images or a single scanned image.

In yet another aspect, the transfer member is treated to enhance the image on the transfer member.

In still another aspect, the transfer member and/or the external body portion may be treated so that when the transfer member is removed from the external body portion an increased amount of material is transferred to the transfer member.

In yet another aspect, the external body portion and/or the transfer member could be analyzed with various types of analysis equipment. In addition, a trained person, such as a clinician, could conduct an analysis of the external portion.

In an even further aspect, the process could include providing a grade indicative of the condition of the external portion and/or the performance of the product, and information relating to this grade could be stored in a database.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate various aspects of embodiments of the process according to the invention and, together with the description, serve to explain the principles of the invention. In the drawings.

FIG. 10a is a view of a scanned image showing pigment spots on skin, wherein data for the image was obtained according to the direct scanning mode of FIG. 8;

FIG. 10b is a view of a scanned image similar to that of FIG. 10a, wherein contact oil has been placed on the spot prior to scanning;

FIG. 11 is a view of a scanned image of skin including pigmentation and micro cuts, wherein data for the scanned image was obtained in a manner similar to that shown in FIG. 8;

DETAILED DESCRIPTION OF EMBODIMENTS

Figure 1:
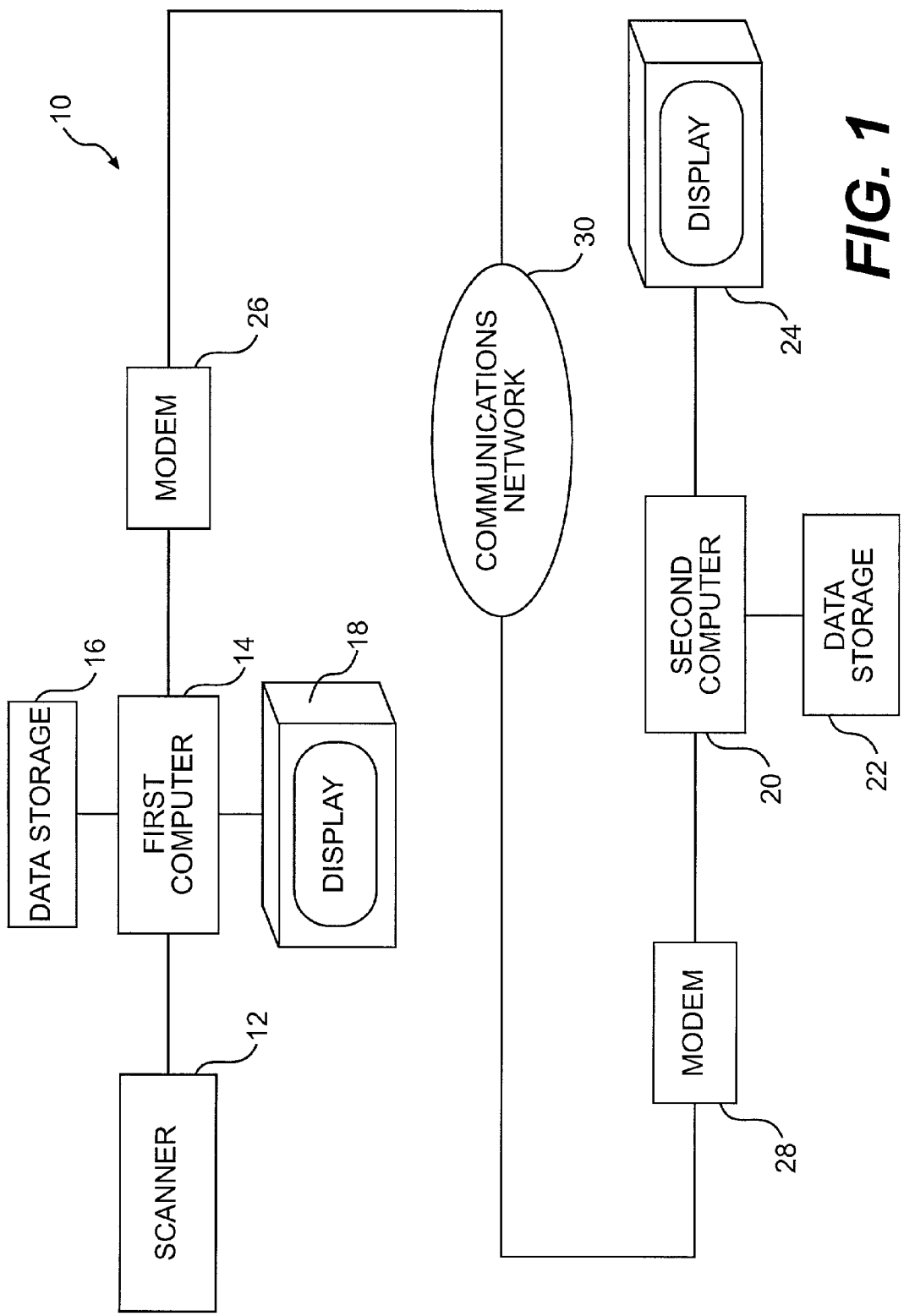
FIG. 1 is a schematic view of an example of system capable of being used to practice the process of the present invention.

Reference will now be made in detail to embodiments of the invention, examples of which are illustrated in the accompanying drawings. Wherever possible, the same reference symbols are used in the drawings and the description to refer to the same or like parts.

FIG. 1 shows an example of a system 10 that could be used to practice a process according to the present invention. The system 10 includes an optical image scanner 12, a first computer 14 associated (via any type of communication link, including a phone line) with the scanner 12, a data storage 16 for the first computer 14, and a visual display screen 18 for the first computer 14. The system 10 also includes a second computer 20 linked to a data storage 22 and a visual display screen 24. Preferably, the optical image scanner 12 and first computer 14 are provided at a first location remote from a second location where the second computer 20 is located. Respective modems 26 and 28 are provided to link communication between the computers 14 and 20 via a communication network 30, such as the Internet.

The first and second computers 14 and 20 could be configured in many different ways. In one implementation, the computers 14 and 20 are conventional personal computers typically found in home or office environments. Many other types of devices, including those that are hand-held, may also be used as long as they are capable of processing scanned image data generated by an image scanner.

One of the initial stages of the process according to the present invention involves obtaining scanned image data with the optical image scanner 12. Preferably, the optical image scanner 12 is a conventional, optical, image scanner typically used to scan documents and/or photographs in a home or office environment. Many different types of commercially available image scanners could be used in the practice of the present invention. For example, the scanner could be a flat bed scanner, a hand-held scanner, a slide scanner, or even a combined scanner and facsimile device. Preferred scanners have a resolution high enough to produce a 2-dimensional scanned image showing viewable details that are normally taken into account during analysis of the condition of an external portion of an individual. For example, the image scanner 12 could have a resolution of up to about 4800 dots per inch (dpi).

Scanners for use in the process of the present invention preferably emit light on an object being scanned. The object being scanned may absorb part of this light, reflect part of it, and/or permit passage of part of it through the object. The scanner preferably detects the reflected portion of light. The emitting of light during scanning enables the scanned image to be relatively standardized and relatively unaffected by ambient light conditions because preferably all, or a substantial portion, of the light detected by the scanner originates from the scanner.

Preferably, the scanner 12 includes one or more light-emitting scanning elements that are moved relative to the object being scanned. Alternatively, the scanner 12 could be configured such that the object being scanned is moved relative to the light-emitting scanning elements. Rather than providing an instantaneous scan of an entire object being scanned, the scanner 12 is preferably configured to sequentially scan different portions of an object in either a block-by-block, line-by-line, or point-by-point manner, for example.

The preferred scanner may have a relatively short depth of field for its scanning (i.e., the scanner and the object being scanned are preferably located at a close, predetermined distance to one another during scanning). In one preferred embodiment, the object being scanned is placed in contact with a support during scanning. For example, the support could be part of the scanner, such as a window defining a scanning region, or the support could be separate from the scanner.

The preferred scanner is also preferably a color scanner configured to produce scanned image data including color data. A color scanner is preferred because it enables a skin diagnosis, for example, that takes into account color. One possible scanner, used to produce the scanned images shown in the drawings, is an EPSON Perfection, model 1200 Photo scanner having a maximum resolution of 1200 dpi. Another type of possible scanner is a QUBYX Lynx A3 scanner having a resolution of between 2400 and 4800 dpi.

Figure 5:
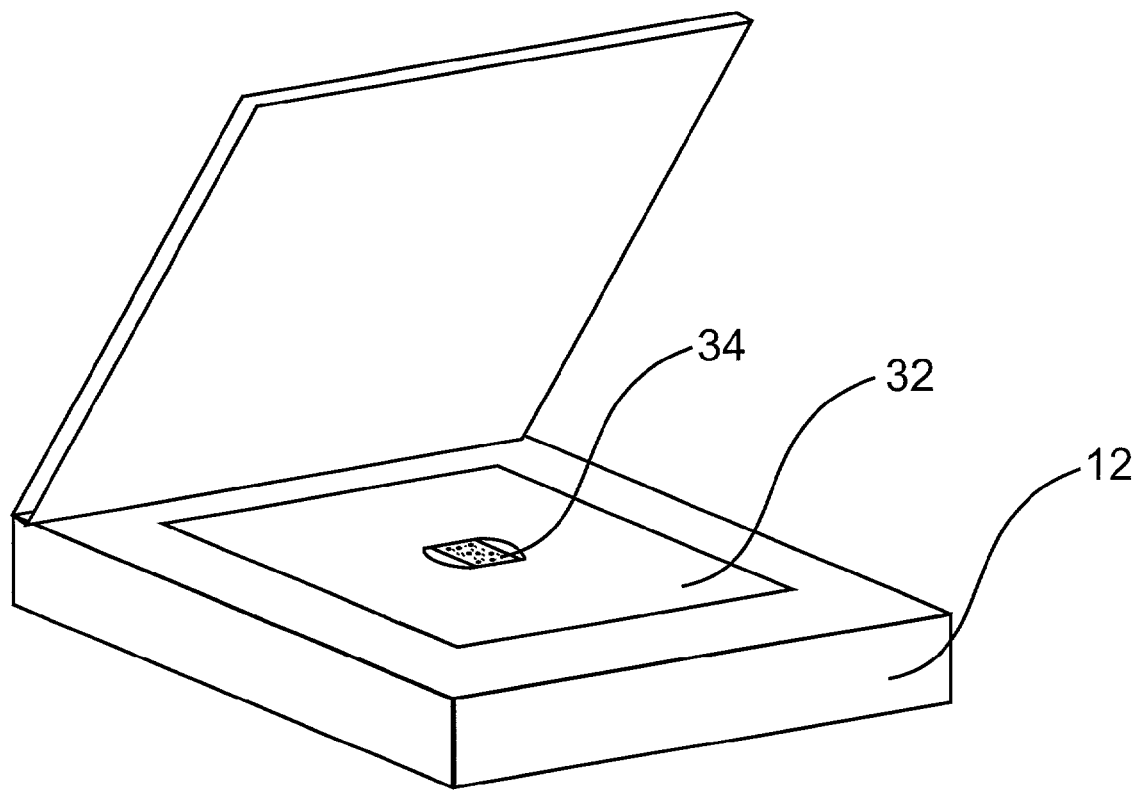
FIG. 5 is a perspective view of scanned image data being obtained by scanning the transfer member of FIG. 4 with a scanner shown in FIG. 1.

In accordance with the present invention, scanned image data is acquired by placing a transfer member in contact with an external portion of an individual to provide an image on the transfer member, and then scanning the image of the transfer member with the scanner to obtain the scanned image data. There are many different types of transfer members that could be used. For example, the transfer member could include either adhesive material provided on a backing, a sheet of absorbent material, a piece of fabric, an article of fabric clothing (i.e., a blouse), a piece of moldable material, a hair brush or comb, or even a portion of the scanner 12, such as a window defining a scanning region 32, as shown in FIG. 5.

Figure 2:
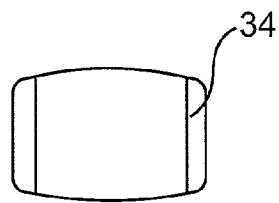
FIG. 2 is a plan view of an adhesive transfer member configured to be used to obtain scanned image data.
Figure 3:
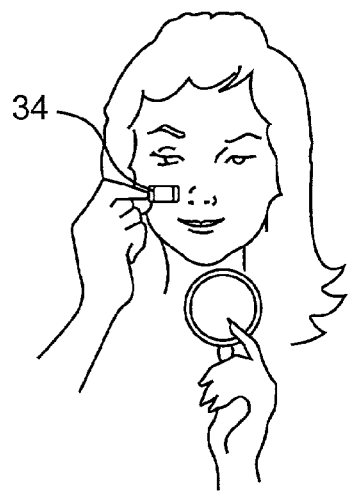
FIG. 3 is a schematic view showing the adhesive transfer member of FIG. 2 being placed in contact with facial skin of an individual.
Figure 4:
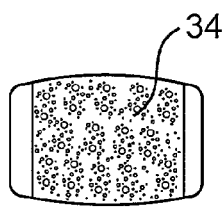
FIG. 4 is a plan view of the adhesive transfer member of FIG. 3 showing skin cells transferred to the transfer member after removal of the transfer member from the skin.
Figure 6:
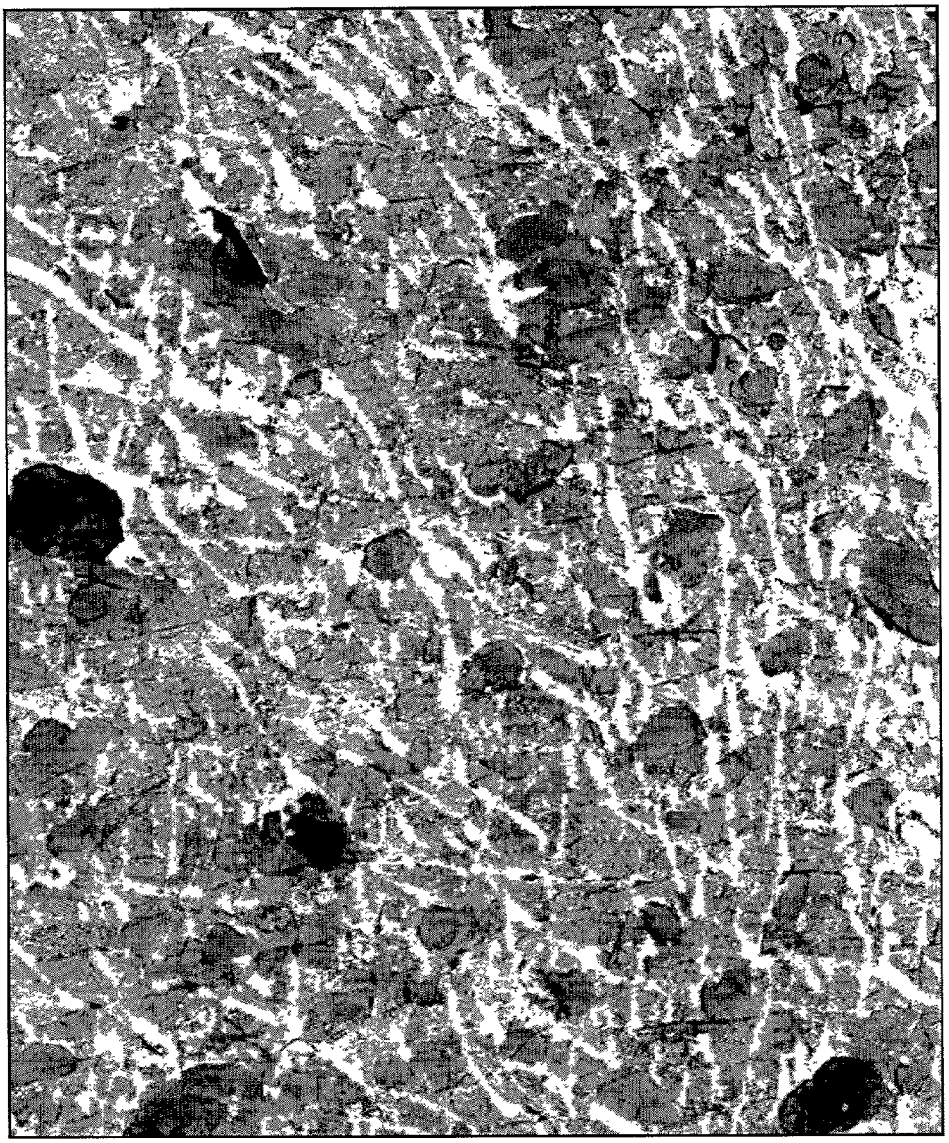
FIG. 6 is a view of a scanned image of skin cells transferred to a transfer member, wherein data for the scanned image was obtained in the manner shown in FIG. 5.

FIG. 2 shows an example of a transfer member 34 including adhesive material provided on a backing. In one preferred embodiment of the invention, the transfer member 34 is a commercially available product called SEBUTAPE. Many other types of alternative configurations are also possible. For example, this type of transfer member could simply be a piece of relatively transparent plastic tape, such as SCOTCH tape manufactured by 3M. As shown in FIG. 3, the adhesive material of the transfer member 34 is placed in contact with skin (i.e., of the face) and, as shown in FIG. 4, when the transfer member is removed from the skin, skin cells and possibly also sebum are transferred from the skin of the individual to the transfer member. As shown in FIG. 5, the transfer member 34 is then scanned with the scanner 12 (for example, by placing it in contact with a glass window pane defining the scanning region 32) to obtain a scanned image showing the transferred skin cells and/or sebum. An example of this type of scanned image is shown in FIG. 6, wherein open areas between aggregates of skin cells show cohesion between the skin cells, separation of skin cells, and valleys in the skin. With such an arrangement, the amount of cells transferred to the transfer member could be analyzed to diagnose the condition of the dryness of the skin. In addition, this could be used to diagnose desquamation.

When the removal of the transfer member 34 from the skin results in a significant amount of skin cells and/or sebum being transferred to the transfer member 34, the amount may be reduced by placing the adhesive side of the transfer member 34 in contact with the adhesive of another transfer member and then separating the two transfer members to transfer amounts of the skin cells and/or sebum to both transfer members.

Such a procedure could be used in order to diagnose the size of individual cells where an overabundance of cells on the transfer member make the analysis difficult.

Figure 7:
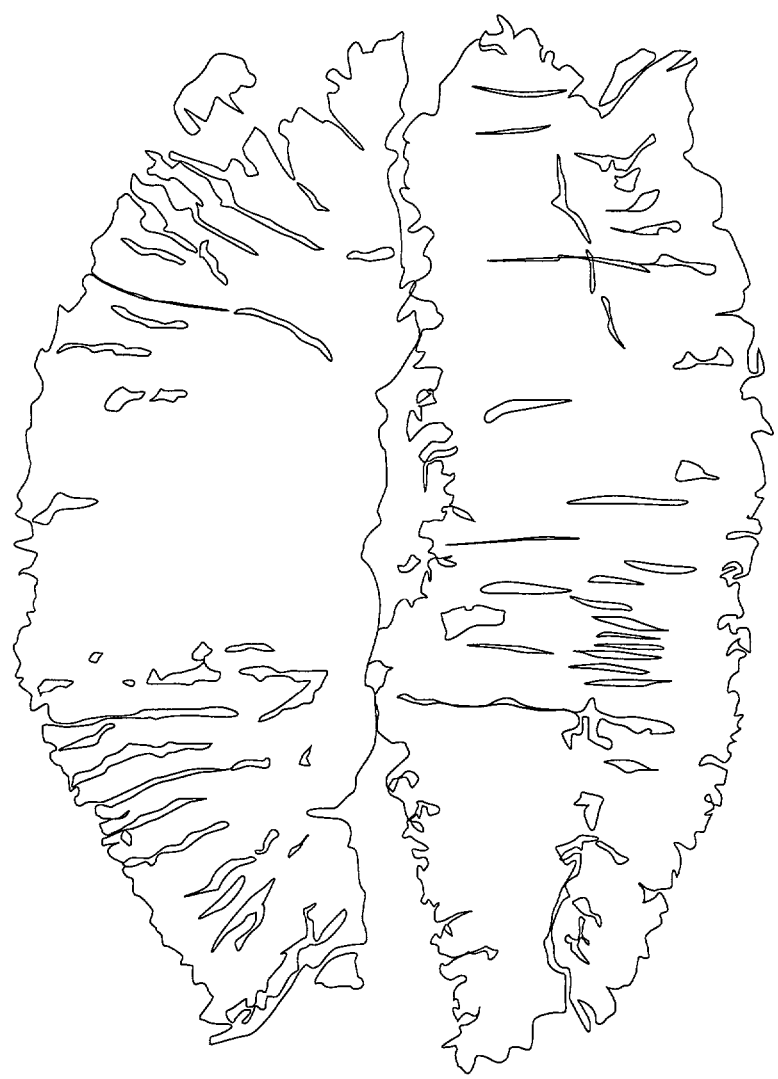
FIG. 7 is a view of a scanned image of a tissue paper transfer member including a lipstick imprint of lips, wherein data for the scanned image was obtained in a manner similar to that shown in FIG. 5.

In an example of the process, a transfer member may be placed in contact with an external body portion having a product, such as a cosmetic product, applied thereto, so that a transfer image relating to one or more characteristics of the product is created on the transfer member. For example, the external portion could include the lips and the product could be a lip care product or a lip makeup product, such as lipstick. One possible type of transfer member is a sheet of absorbent material and this sheet could be in the form of a paper sheet, such as a facial tissue, toilet tissue, or paper towel. The sheet of material could be placed in contact with lips of an individual to transfer a lip product, such as lipstick, from the lips to the sheet of material. FIG. 7 shows an example of a scanned image of tissue paper including an imprint of lips formed, for example, from lipstick. This type of scanned image could be used to diagnose the non-retention and/or non-transferability characteristics of lipstick over time. In other words, the process could be used to determine the ability of the lipstick to remain on the lips as a function of time and/or as a function of the number of events when the lips come in contact with other things, such as by kissing. Additionally, such a process could be used to determine coverage of the product on the external body portion.

In another example, a transfer member in the form of a piece of fabric or an article of fabric clothing (i.e., a blouse) could be placed in contact with skin, such as facial skin, having foundation makeup applied thereto. The amount of any foundation makeup transferred to the transfer member could then be scanned with the scanner 12. Such a process could be used to analyze non-retention and/or non-transferability characteristics of the foundation makeup. In particular, the method could be used to evaluate whether a product causes soiling of clothing and/or whether the product remains on the skin during a period of time.

In a further example, the transfer member includes a moldable material, such as modeling clay or a malleable paste. The moldable material could be pressed against the surface of the skin to produce the surface profile of the skin on the moldable material. The moldable material could then be scanned to produce a scanned image. Such a scanned image could be used for the analysis of micro-reliefs in the skin.

In still another example, the transfer member could be the window of the scanning region 32. In such an arrangement, a visible image would be created on the window after contact of an external body portion with the window, and removal of the body portion prior to scanning. For instance, a lip imprint like that of FIG. 7 could be placed on the window, for example with lipstick. This could be used in the analysis of the non-transferability of a lip product.

The process of the present invention could be practiced to determine both the coverage and non-transferability of a product applied to the external body portion. For example, after applying a cosmetic product to a skin portion, the skin portion could be placed in contact with the scanning region 32 during scanning to obtain image data for an image representing coverage (i.e., homogeneity) of the product on the skin portion. After removing the skin portion from the scanning region 32, any of the product transferred from the skin portion to the scanning region 32 (which is also the transfer member in this example) could then be scanned to obtain scanned image data for an image relating to the non-transferability of the product.

A hair brush or a hair comb could also provide a transfer member. With this type of an arrangement, the brush or comb would be passed through the hair to collect hair strands and/or skin cells and then the brush or comb would be scanned in a manner like that of FIG. 5. This could be used to diagnose the extent of hair loss or dandruff, for example.

In an alternative process according to the invention, the transfer member may be configured to change color when the transfer member is placed in contact with the external body portion and the color change may provide an indication of the condition of the external body portion. For example, the transfer member could be configured in the form of litmus paper capable of measuring PH of the skin by changing color.

Optionally, the transfer member and/or the external body portion could be treated before the transfer member is placed on the external body portion. Such treatment might enhance gathering of material on the transfer member and/or viewing of features on the transfer member.

Figure 8:
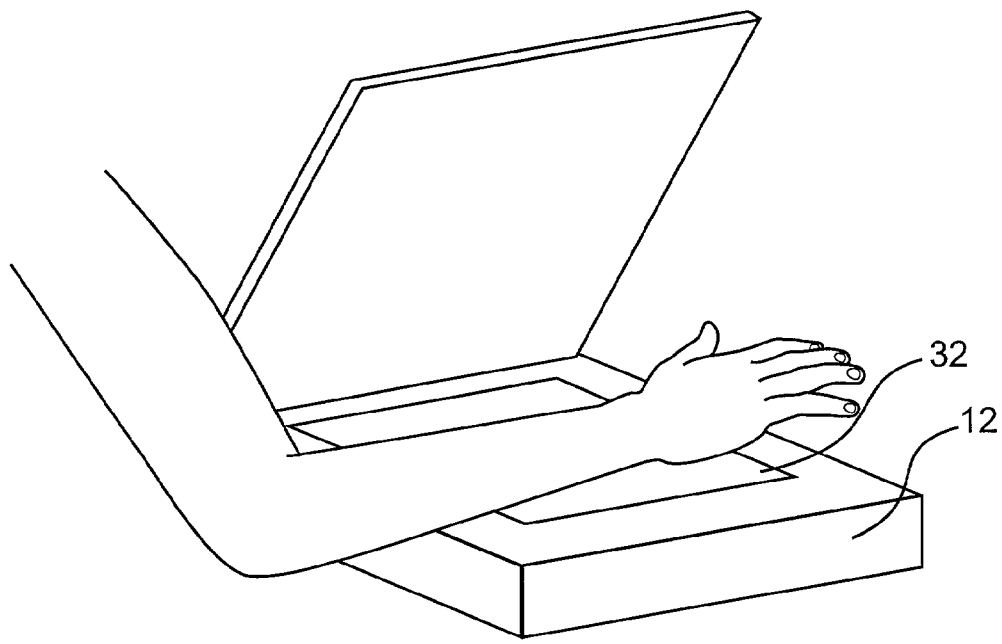
FIG. 8 shows a schematic view of scanned image data being obtained by directly scanning an external portion of the body with the image scanner shown in FIG. 1.

In addition to using the transfer member to acquire scanned image data, scanned image data may also be acquired in other scanning modes. FIG. 8 shows an example of the direct scanning mode. In the direct mode, the external portion of an individual (i.e., the arm shown in FIG. 8) is placed in the vicinity of a scanning region 32 of the scanner, and the external portion is scanned with the image scanner 12 to obtain scanned image data. In the example shown in FIG. 8, the scanner 12 includes a scanning region 32 configured in the form of a glass window pane that makes contact with an object being scanned, the external portion of the individual is preferably placed into contact with this scanning region 32 during the scanning. Preferably, the scanner shown in FIG. 8 is a flat bed scanner, and the external portion of the individual is moved into contact with the glass window pane of the scanner 12. If, on the other hand, the scanner is a hand-held scanner (not shown), the scanner can be moved to place its scanning region into contact with the external portion of the individual.

The direct scanning mode and the scanning mode using the transfer member could be combined in a number of different ways to obtain scanned image data relating to an exterior portion of a body. For example, both a transfer member and an external body portion could be placed in contact with the scanning region 32 and then scanned substantially simultaneously. Alternatively, scanning in the different modes may occur one after the other so that scanned image data from both of these modes may be used.

In one example of a process combining multiple modes and analysis of both external portion characteristic and product characteristics, skin of the cheek could be placed in contact with the scanning region 32 during scanning to obtain image data relating to an image representative of normal transparency of the skin. Then, a hydrating cream that improves skin transparency could be applied to the cheek and cheek could be again scanned while in direct contact with the scanning region 32 to obtain scanned image data relating to the improved visibility provided by the cream. After the cheek is finally removed from the scanning region 32, any cream transferred to the scanning region 32 (i.e., the scanner window provides the transfer member) could then be scanned to obtain scanned image data relating to non-transferability of the cream.

Figure 9:
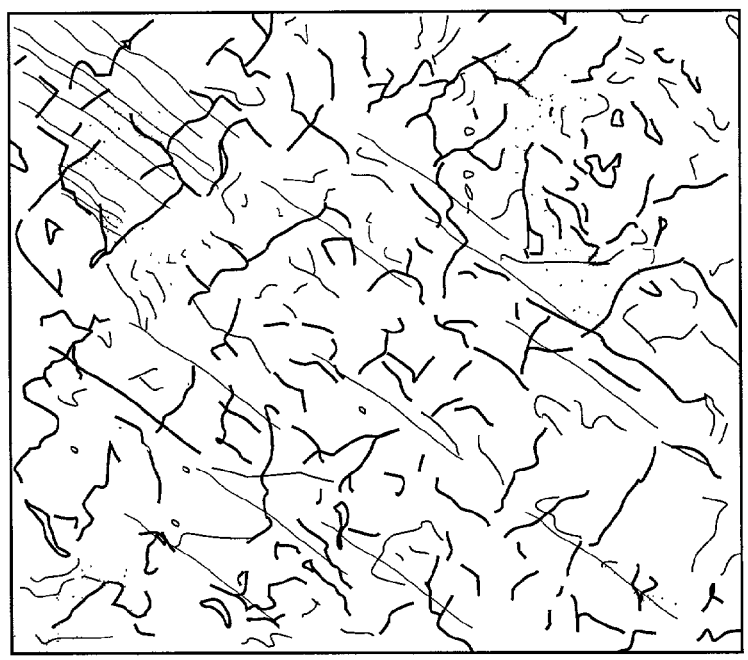
FIG. 9 is a view of a scanned image showing dry skin from a leg, wherein data for the image was obtained according to the direct scanning mode of FIG. 8.

The direct scanning mode could be used for the diagnosis of a skin condition. For example, when diagnosing a skin condition, such as dry skin, the skin of an individual's face, arm, leg, hand, foot, or torso could be brought in the vicinity of (i.e., placed near or against) the scanning region 32 of the scanner 12 during scanning. FIG. 9 shows an example of a scanned image showing dry skin from a leg, wherein the image was scanned while the scanning region 32 was in contact with the skin. The direct mode scanning might also be used in the diagnosis of many other skin conditions, such as psoriasis, vitiligo, or melanoma, for example.

Scanning in the direct mode could also be used to diagnose certain pigmented areas on the skin and/or blood vessels, such as micro vessels, visible through the skin. FIG. 10a shows an example of a direct mode scanned image showing a skin region containing pigment spots P and a visible micro vessel MV. FIG. 10b is an example of a scanned image showing the skin region of FIG. 8a wherein a liquid (i.e., contact oil) has been placed on the spot prior to scanning in order to alter the index of refraction and thereby improve viewing of the skin characteristics, such as the pigment spots P and the micro vessel MV. This aspect of the process may be used to diagnose the condition of blood vessels visible through the skin and to detect acrosyndromes or couperosis, for example.

To further enhance viewing, a dye and/or pigment (i.e., a fluorescent pigment) could be placed on the skin prior to the scanning.

Figure 12:
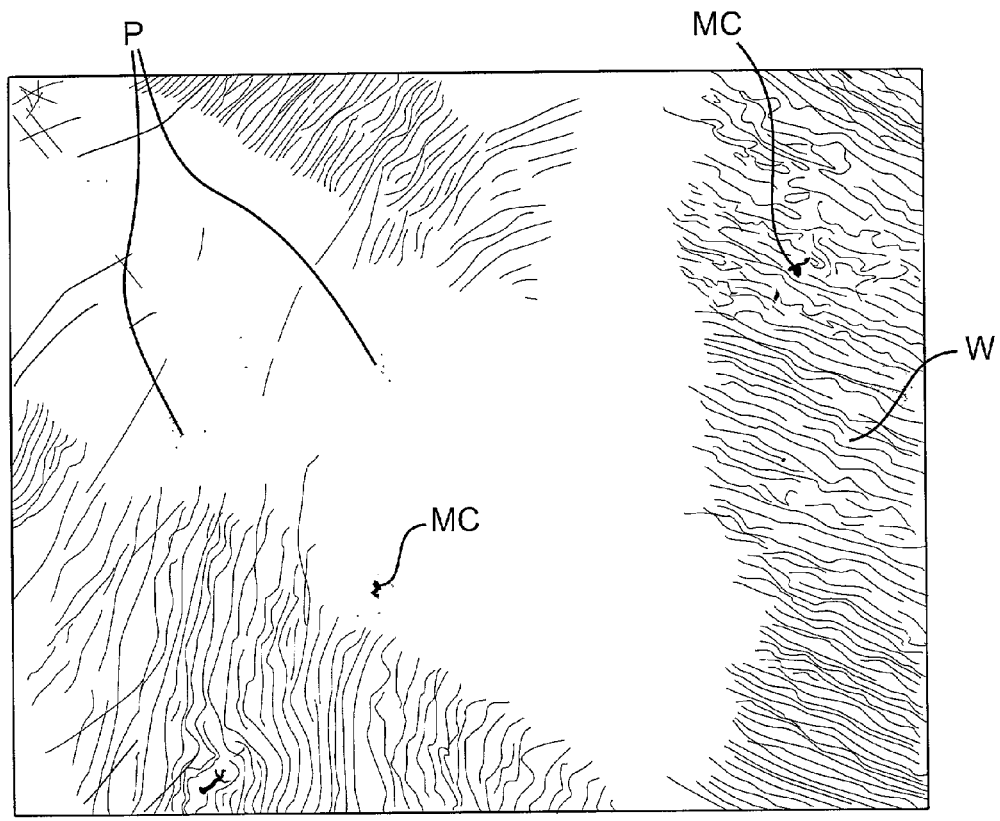
FIG. 12 is a view similar to that of FIG. 11 showing skin from another external portion of the body, wherein data for the scanned image was obtained in a manner similar to that shown in FIG. 8.

FIG. 11 is an example of another direct mode scanned image showing a skin region including pigment spots P and micro-cuts MC caused, for example, by shaving. FIG. 12 is another example of a direct mode scanned image showing a skin region similar to that of FIG. 11 and also including wrinkles W.

Figure 13:
FIG. 13 is a view of a scanned image showing dry skin, wherein data for the scanned image was obtained in a manner similar to that shown in FIG. 8.
Figure 14:
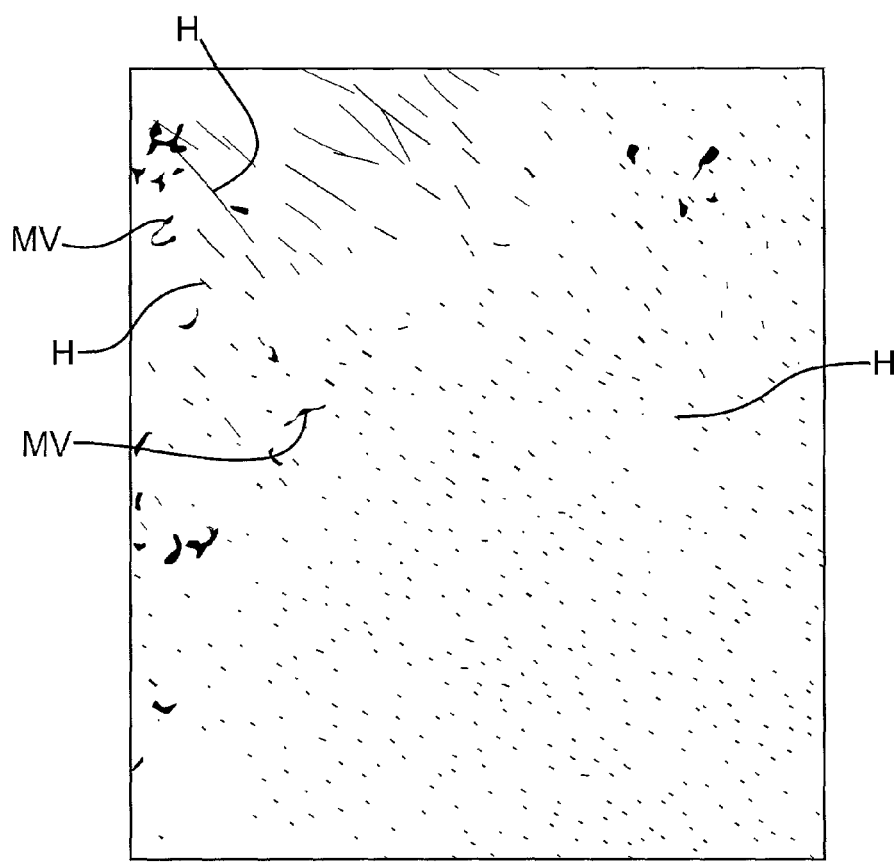
FIG. 14 is a view of a scanned image of skin of the cheek showing small micro vessels and facial hair, wherein data for the scanned image was obtained in a manner similar to that shown in FIG. 8.

FIG. 13 is an example of a direct mode scanned image showing a skin region having cracks indicating a significant number of dry and/or dead skin cells. FIG. 14 shows another example of a direct mode scanned image of a skin region from an area such as the cheek, wherein the skin region includes micro vessels MV and a number of facial hair strands H, some of which have been shaved shorter than others.

Figure 15:
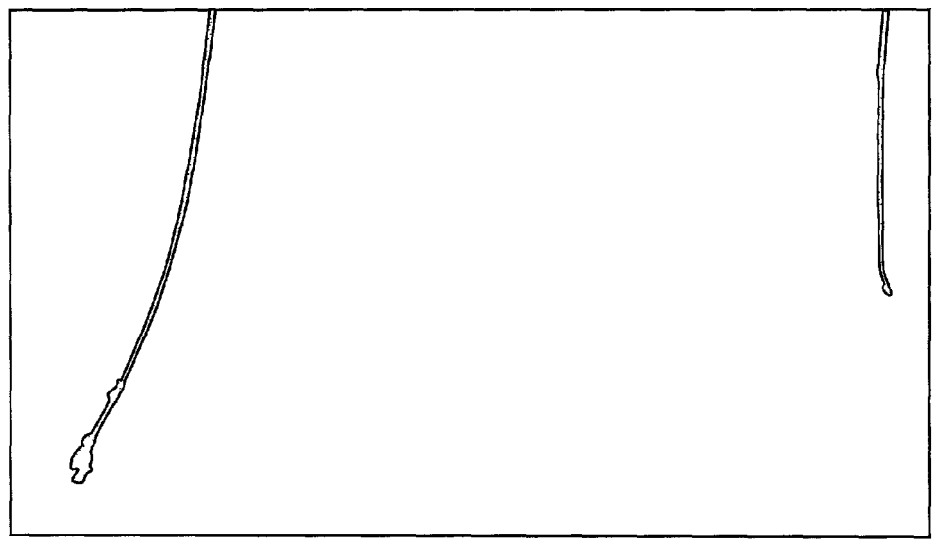
FIG. 15 is a view of a scanned image of root portions of two strands of hair, wherein data for the image was obtained according to the direct scanning mode of FIG. 8.
Figure 16:
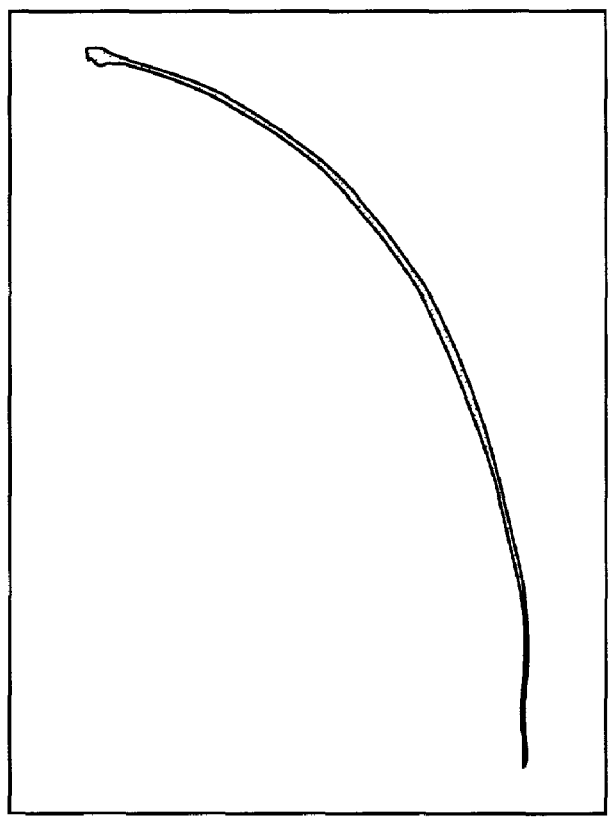
FIG. 16 is a view of a scanned image of an entire strand of hair, wherein data for the image was obtained according to the direct scanning mode of FIG. 8.

In addition to being used in analysis of skin, the direct mode could also be used to scan the image of a strand of hair for use in the diagnosis of certain hair conditions, such as determining the thickness or length of a strand of hair or the status of a hair root. For example, the strand could be either a strand of hair from the scalp of the individual, an eyelash of the individual, or an eyebrow hair of the individual. FIG. 15 shows an example of a scanned image of the root portions of two separate strands of hair. FIG. 16 shows an example of a scanned image of an entire strand of hair. Each of the images of FIGS. 15 and 16 was scanned while the hair strand was placed against the scanning region 32.

The hair strands shown in FIGS. 15 and 16 could be obtained in a variety of different ways. For example, the hair strands could be pulled from the skin of the individual, removed during brushing or combining, or collected from clothing or a drain of a shower or bath.

Figure 17:
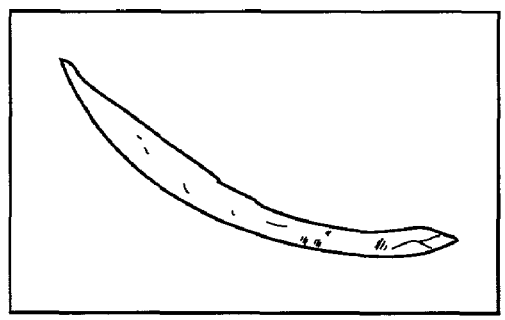
FIG. 17 is a view of a scanned image of a nail clipping of a fingernail, wherein data for the image was obtained according to the direct scanning mode of FIG. 8.
Figure 18:
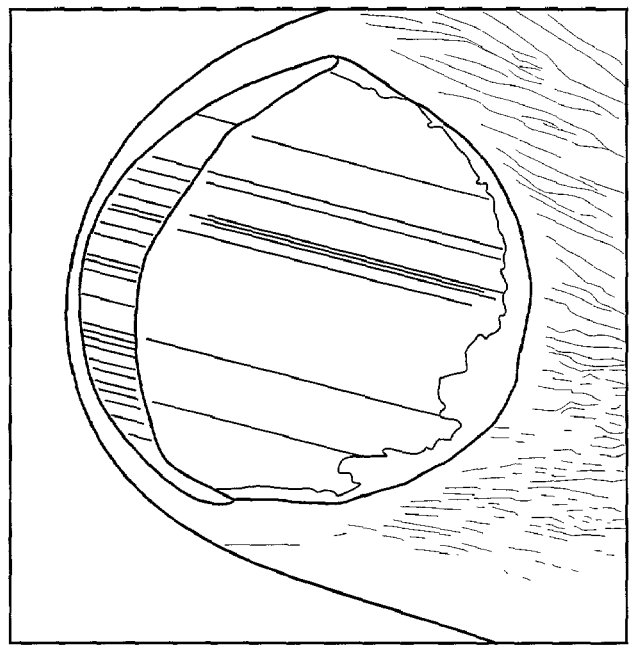
FIG. 18 is a view of a scanned image of a finger tip showing a fingernail, wherein data for the image was obtained according to the direct scanning mode of FIG. 8.
Figure 19:
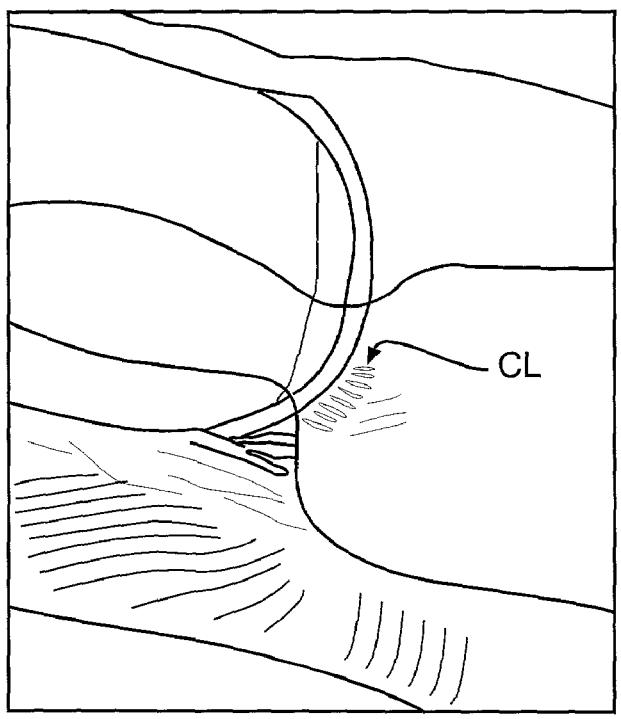
FIG. 19 is a view of a scanned image of a nail showing bed capillaries, wherein a liquid is used to modify the index of refraction and wherein data for the image was obtained according to the direct scanning mode of FIG. 8.

The direct scanning mode could also be used to scan an image of a fingernail or a toenail for use in diagnosis relating to pathology, ungual state, onychomycosis, or split nails, for example. FIG. 17 shows an example of a scanned image of a nail clipping of the fingernail, wherein the image was obtained by scanning when the nail clipping was in contact with the scanning region 32. A scanned image like that of FIG. 17 may be used in the diagnosis of nail delamination. FIG. 18 shows an example of a scanned image showing a fingernail and cuticle, wherein the image was obtained by scanning when the finger tip was in contact with the scanning region of the scanner. FIG. 19 shows a scanned image similar to FIG. 18, wherein a liquid (i.e., oil) was placed on the finger prior to scanning to improve visualization of capillary loops CL near the cuticle of the finger. Such an image could be used for the diagnosis of acrosyndromes, such as Raynaud's syndrome.

Figure 20:
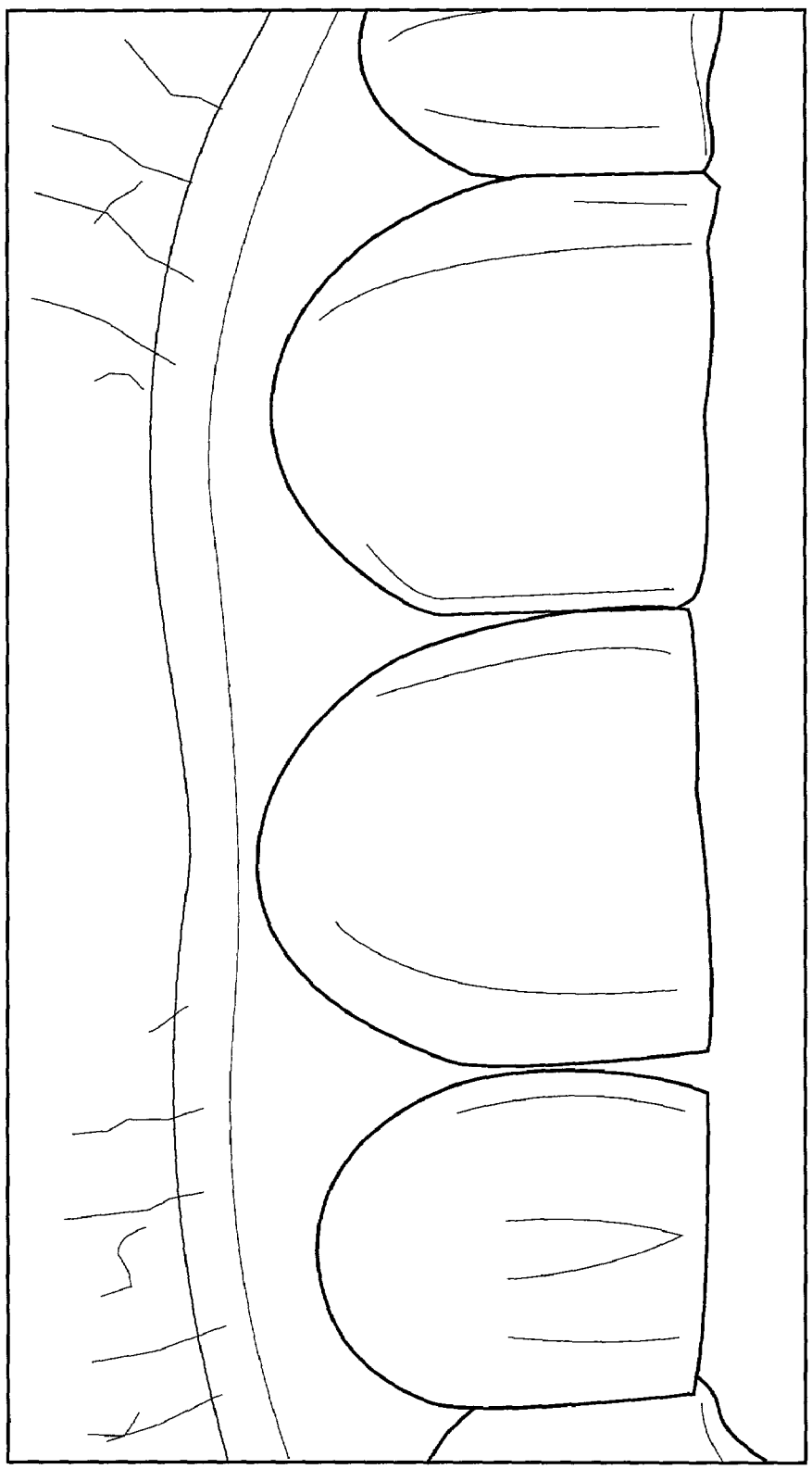
FIG. 20 is a view of a scanned image of top, front teeth, wherein data for the scanned image was obtained in a manner similar to that shown in FIG. 8.

The direct mode scanning could also be used to scan other exterior portions of the body. For example, FIG. 20 shows an example of a scanned image of top front teeth. Such an arrangement could be used to diagnose a number of different conditions of the teeth.

Optionally, a calibration member may be scanned along with the transfer member and/or external body portion. For example, the calibration member could have a predetermined size and or color that would enable calibration of an image formed from the scanned image data (for example, via image processing software such as Photoshop) to provide a more exact indication of the size and/or color of characteristics.

When the scanned image data has been obtained, the process according to the present invention could further include analyzing one or more characteristics of the external body portion and/or the product applied thereto, and determining a diagnosis of one or more conditions of the external portion and/or one or more features of the product. There are many different ways in which this analysis and determination may take place. For example, the analysis could include a person viewing an image (displayed on the first or second display screen 18, 24 for example) formed from the scanned image data obtained with the image scanner 12, and making a determination of a diagnosis based on this viewing. Alternatively, a computer program running on the first or second computer 14, 20 could perform at least a portion of the analysis and diagnosis. The person and/or computer performing the analysis and/or diagnosis could provide a grade indicating the condition of the external portion and/or product performance, and this grade could be stored in one of the data storages 16, 22.

The analysis according to the present invention could combine both an analysis of one or more images formed from the scanned image data and any other type of analysis for external body portions and/or cosmetic products. For example, the other analysis could be an analysis using conventional analysis equipment used for analyzing external body portions and/or cosmetic products applied to external body portions. In particular, the process could include usage of equipment typically used by specialists during examinations. For example, the process of the present invention could include the use of corneometer, a dermal torque meter, an image analyzer, a sebumeter, a PH meter, or a device for measuring hydration of the skin. The other analysis could also be an analysis performed by a trained person, such as a clinician, directly viewing the external portion, for example, at a location where products are sold. The additional analysis could be used to confirm the results of the analysis via the scanned image data. During the course of this analysis, a grade representative of the condition of the external portion and/or performance of the product could be provided. This grade could then be stored, for example, in one of the data storages 16, 22.

In one preferred practice of the present invention, the scanned image data is transferred from the first computer 14 to the second computer 20 via the communications network 30. Alternatively, the data could be stored on a data storage medium, such as a computer disk, CD, or other information storage means, and this data storage medium could be shipped to the location of the second computer 20. In addition, the scanned image data could be stored in the first and/or second data storages 16, 22.

Optionally, the scanned image data could be transferred to the second computer 20 along with written information, such as answers to a brief questionnaire regarding the condition of the exterior body portion and/or any product applied to the external portion. These questionnaire answers may then be considered in conducting the analysis and diagnosis. In addition, billing information and/or payment information may also be sent along with the scanned image data.

Preferably, the second computer 20 is located at a diagnosis area where an image can be created from the scanned image data transferred from the first computer 14. Optionally, this image could be displayed at the second location on the second display screen 24. The image preferably contains representations of one or more of the characteristics of the external body portion and/or the product applied to the external portion. These characteristics are analyzed at the second location to provide a diagnosis of one or more conditions of the external portion and/or one or more features of any product applied to the external portion. At least part of the analysis could involve a person viewing a displayed image at the second location. In addition, some or at least substantially all of the analysis could be performed automatically by the second computer 20. For example, the image could be analyzed at least partially by means of an image analysis software operating on the second computer 20.

Optionally, the first computer 14 and/or the second computer 20 could modify the scanned image data to improve the viewing of certain characteristics of the external body portion and/or the product. For example, image modification software, such as Photoshop, could be used to enhance viewing of the characteristics shown in the images. Such software could be used to digitally magnify portions of images being displayed to facilitate analysis and diagnosis.

Preferably, the results of the diagnosis are provided to the individual and/or a treatment provider for the individual. For example, the diagnosis could be sent via the communications network 30.

When one or more conditions of an individual's external portion have been diagnosed, a recommendation for treatment of the condition(s) may be determined. Preferably, this recommendation is provided to the individual and/or a treatment provider so that the external portion of the individual may be treated according to the recommendation.

The recommendation could be determined at least in part by a manual process or an automated process. For example, the recommendation could be determined by selecting, from one of the data storages 16 and 22, treatments based on the diagnosed condition. The recommendation could be provided to the individual and/or treatment provider by sending it via the communications network 30. In addition, information relating to the diagnosis could also be provided along with the recommendation.

In one aspect of the present invention, the recommendation is a recommendation regarding use of at least one of a cosmetic product and a dermatological product. A wide variety of products could be recommended using the technique. For example, the recommended products may be chosen from makeup products, care products (both therapeutic and non-therapeutic), hair products, skin products, and sun exposure products (i.e., sun screen or after-sun products). The recommendation could be a prescription for a particular product.

The treatment recommendation may include a recommendation regarding application of a product to the external portion. Optionally, product ordering information may be provided along with the recommendation.

In certain circumstances, the treatment recommendation might not involve usage of a particular product. For example, the treatment recommendation could be advice regarding hygiene or cleaning for a body portion.

The scanned image information transferred from the first computer 14 to the second computer 20 could also be used for monitoring the status of the condition of the external portion during treatment. For example, skin pigmentations could be monitored over time to determine effectiveness of a treatment; or sizes of skin cells could be monitored over time to determine skin cell renewal rate. Optionally, an additional recommendation for a treatment could be provided based on the monitored status. Such a recommendation could be a recommendation regarding application of at least one cosmetic product and dermatological product to the external portion, and product ordering information can be provided along with the recommendation. In addition, the process could involve providing the individual with information regarding the effectiveness of the recommended treatment. The monitoring could include repeating the obtaining of the scanned image data and the analysis. Each monitoring could include providing a grade representative of the condition of the external portion and/or product performance.

One more additional aspect involves collecting information relating to the scanned external portion to form a database for use in at least one of further diagnoses, further recommendation determinations, further product evaluations, and/or product formulations. For example, a neural network could be established that would add information to its database and establish some form of artificial intelligence system. Such a database could be used when conducting further analysis of characteristics of external body portions and/or products. For example, an image formed from the scanned information could be compared to an image formed from a database stored in one of the data storages 16 and 22. The database could also be used to evaluate different product formulations to select an appropriate formulation. Optionally, the database could include information relating to one or more grades representative of the condition of the external portion and/or product performance.

Another possible practice of the present invention involves sending the scanned image data to a plurality of different locations, for example via the communications network 30, to permit substantially simultaneous analysis at a plurality of different areas. For example, such a practice of the present invention could permit a team of experts in different areas to diagnose external body conditions and/or evaluate products, such as cosmetic products, somewhat simultaneously.

The process of the present invention could be practiced to diagnose many different types of conditions. For example, the process could be practiced to diagnose skin conditions, such as elasticity, dryness, cellulitis, sweating, aging, wrinkles, melanoma, exfoliation, desquamation, homogeneity of color, micro-circulation, shininess, softness, smoothness, matitty, hydration, sebum production, cleanliness, irritation, redness, vasomotion, vasodilation, vasoconstriction, pigmentation (including freckles), PH, whitening, dying or coloring, insect bites, growths, lesions, wounds, post surgical incisions, wound healing, etc., for example.

With regard to hair, the process may be practiced to diagnose dying, curling, scales, keratin plugs, length, dryness, oiliness, dandruff, lice or other parasites, thickness, density, root conditions, split ends, hair loss, staging, etc., for example.

For fingernails or toenails, the process could be practiced to diagnose lines, spots, thickness, skin at the base of the nail, delamination, curvature, brilliancy, length, psoriasis, etc., for example. In addition, diagnoses relating to the teeth may include color, enamel coverage, surface smoothness, whiteness, etc., for example.

When the process involves a treatment recommendation for the external portion, there are a variety of different treatment recommendations that could be provided. For example, treatment recommendations for skin conditions could include use of nourishing cream, anti-wrinkle cream, moisturizer, or keratinous cream; applying a solution of salicylic acid; or removal of dead skin cells via exfoliation, etc., for example. Possible hair treatment recommendations may include use of special shampoos or other products for treating hair loss, split ends, dandruff; or types of hair trimming, etc., for example.

For nails, possible treatment recommendations include, pushing of the cuticles, applying cuticle cream, softening of the cuticles, polishing nails, use of nail varnish, application of nail care creams (i.e., for treating psoriasis), etc. for example. Regarding the teeth, possible treatment recommendations relate to brushing, flossing, and use of whiteners, tart removers, or nicotine removers, etc., for example.

The process according to the present invention could preferably have a number of different advantages. For example, the process preferably could obtain an image with a very high resolution as long as the scanner has that capability. Commercially available document scanners have resolutions up to 4800 dpi, for example. Such high resolutions are greater than those of conventional photographs, and not obtainable with a simple direct viewing of an external portion through a magnifying glass.

The invention could preferably be practiced with equipment typically available to most Internet users.

When a color scanner is used, the color image allows for very accurate diagnosis of color related conditions.

The use of a scanner is advantageous because lighting can be automatically standardized with this type of digitizer. The external portion or transfer member can be scanned by directly placing it in contact with the scanning region, for example, and directly acquiring, point by point, calorimetric coordinates of the image. This is not the case with pictures (either film-based or digital) produced in a home or professional setting.

One other relatively significant advantage relates to the fact that the images are directly transferable to a cosmetician or dermatologist electronically, preferably without any manipulation.

Another advantage relates to the ability to create the image without regard to the level of external lighting.

A further advantage relates to the ability to monitor the change in pathology or effectiveness of a treatment without having to travel.

Of course, many aspects of the invention could be practiced without necessarily accomplishing one or more of these advantages.

It will be apparent to those skilled in the art that various modifications and variations can be made to the structure and methodology of the present invention without departing from the scope or spirit of the invention. In view of the foregoing, it is intended that the present invention cover modifications and variations of this invention, provided they fall within the scope of the following claims and their equivalents.

What is claimed is:

1. A process for acquiring scanned image data relating to an external body portion and/or a product applied to the external body portion, the process comprising:
   placing a transfer member in contact with an external portion of an individual so as to obtain a transfer image on the transfer member,
   wherein the transfer image is present on the transfer member after the transfer member and the external portion are out of contact with one another,
   wherein the transfer image is not a fingerprint or fingerprints, and
   wherein the external portion that the transfer member is placed in contact with does not include a tooth or teeth; and
   scanning the transfer image with an optical image scanner to obtain scanned image data for an image representative of at least one characteristic of
   the external body portion, and/or
   at least one product applied to the external body portion,
   wherein the image scanner is associated with a first computer located at a first location, and wherein the process further comprises transferring the scanned image data from the first computer to a second computer located at a second location remote from the first location, and
   wherein the image scanner is configured in the form of a scanner for scanning documents.

2. The process of claim 1, wherein the transferring includes transmitting the scanned image data via the Internet.

3. The process of claim 1, further comprising storing the scanned image data on a data storage medium, wherein the transferring includes shipping the data storage medium to the second location.

4. The process of claim 1, further comprising transferring questionnaire answers from the first location to the second location, at least some of the questionnaire answers being related to at least one of a condition of the external portion and the product applied to the external body portion.

5. The process of claim 1, further comprising sending to the second location at least one of billing information and payment information.

6. A process of analyzing at least one characteristic of an external body portion of an individual and/or at least one product applied to the external body portion, the process comprising:
   acquiring scanned image data according to the process of claim 1;
   displaying an image corresponding to the scanned image data; and
   viewing the displayed image to analyze said at least one characteristic.

7. The process of claim 6, wherein the image is displayed at the second location.

8. The process of claim 6, further comprising sending the scanned image data to a plurality of locations so that the at least one characteristic may be analyzed numerous times.

9. The process of claim 6, further comprising monitoring status of the external portion during treatment of the external portion.

10. The process of claim 9, further comprising providing a recommendation for a treatment of the external portion based on the monitored status.

11. The process of claim 9, further comprising providing the individual with information regarding the effectiveness of the treatment.

12. The process of claim 9, wherein the monitoring includes repeating at least the acquiring.

13. A process for recommending treatment for an external body portion, the process comprising:
   analyzing at least one characteristic of an external body portion wherein the analyzing comprises
   acquiring scanned image data, wherein the acquiring comprises
   placing a transfer member in contact with an external portion of an individual so as to obtain a transfer image on the transfer member,
   wherein the transfer image is present on the transfer member after the transfer member and the external portion are out of contact with one another,
   wherein the transfer image is not a fingerprint or fingerprints, and
   wherein the external portion that the transfer member is placed in contact with does not include a tooth or teeth;
   scanning the transfer image with an optical image scanner to obtain scanned image data for an image representative of at least one characteristic of the external body portion, and/or
at least one product applied to the external body portion;
displaying an image corresponding to the scanned image data; and
viewing the displayed image to analyze said at least one characteristic;
determining a recommendation of at least one treatment for the external portion; and
providing the treatment recommendation so that the external portion of the individual may be treated according to the recommendation,
wherein the image scanner is configured in the form of a scanner for scanning documents.

14. The process of claim 13, wherein the treatment recommendation is a recommendation regarding use of at least one of a cosmetic product and a dermatological product.

15. The process of claim 14, wherein said at least one of the cosmetic product and the dermatological product is one of a makeup product, a care product, a hair product, a skin product, and a sun exposure product.

16. The process of claim 14, wherein the treatment recommendation is a recommendation regarding application of said at least one of the cosmetic product and the dermatological product to the external portion.

17. The process of claim 13, further comprising providing product ordering information along with the treatment recommendation.

18. The process of claim 13, wherein the providing of the treatment recommendation includes providing the treatment recommendation to at least one of the individual and a treatment provider.

19. The process of claim 18, wherein the providing of the treatment recommendation includes transmitting said recommendation to said at least one of the individual and the treatment provider via the Internet.

20. The process of claim 13, wherein a computer at least partially performs the determining of the treatment recommendation, the computer being located at a location remote from that of the image scanner.

21. A process for acquiring scanned image data relating to an external body portion and/or a product applied to the external body portion, the process comprising:
placing a transfer member in contact with an external portion of an individual so as to obtain a transfer image on the transfer member,
wherein the transfer image is present on the transfer member after the transfer member and the external portion are out of contact with one another,
wherein the transfer image is not a fingerprint or fingerprints, and
wherein the external portion that the transfer member is placed in contact with does not include a tooth or teeth;
scanning the transfer image with an optical image scanner to obtain scanned image data for an image representative of at least one characteristic of
the external body portion, and/or
at least one product applied to the external body portion; and
collecting information relating to the transfer image of the transfer member to form a database for use in at least one of diagnoses, treatment recommendation determinations, product evaluations, and product formulations,
wherein the image scanner is configured in the form of a scanner for scanning documents.

22. The process of claim 21, further comprising providing a grade indicative of at least one of the condition of the external portion and performance of the product.

23. The process of claim 22, further comprising storing information relating to the grade in a database.

* * * * *